United States Patent [19]
Tobe et al.

[11] Patent Number: 6,060,597
[45] Date of Patent: May 9, 2000

[54] CYCLIC OLIGOSACCHARIDE, AND AN AGENT CONTAINING THE SAME FOR PREVENTING OR TREATING RETROVIRAL DISEASES

[75] Inventors: Koichiro Tobe; Makoto Saito; Shoichi Tokutake, all of Chiba; Satoshi Kitao, Osaka; Tetsuya Oguma, Chiba; Kahee Fujita, Nagasaki, all of Japan

[73] Assignees: Kikkoman Corporation; Noda Institute for Scientific Research, both of Chiba, Japan

[21] Appl. No.: 09/127,126

[22] Filed: Jul. 30, 1998

[30] Foreign Application Priority Data

Jul. 30, 1997 [JP] Japan ................................. 9-205071
Jul. 2, 1998 [JP] Japan ................................. 10-187286

[51] Int. Cl.⁷ ............................ C08B 30/18; C08B 37/16
[52] U.S. Cl. ................................. 536/46; 514/58; 536/124
[58] Field of Search ............................... 514/58; 536/46, 536/124

[56] References Cited

U.S. PATENT DOCUMENTS

| | | | |
|---|---|---|---|
| 2,923,704 | 2/1960 | Berger et al. | 536/103 |
| 4,020,160 | 4/1977 | Bernstein et al. | 514/58 |
| 4,201,772 | 5/1980 | Ingelman et al. | 514/58 |
| 4,247,535 | 1/1981 | Lewis et al. | 514/58 |
| 4,258,180 | 3/1981 | Lewis et al. | 536/112 |
| 5,019,562 | 5/1991 | Folkman et al. | 514/58 |
| 5,221,669 | 6/1993 | Anand et al. | 514/58 |
| 5,248,675 | 9/1993 | Kurita et al. | 514/58 |
| 5,250,520 | 10/1993 | Kurita et al. | 514/58 |
| 5,364,936 | 11/1994 | Oguma et al. | 536/103 |
| 5,385,891 | 1/1995 | Moriya et al. | 514/58 |
| 5,447,859 | 9/1995 | Prussak | 435/239 |
| 5,453,369 | 9/1995 | Oguma et al. | 435/193 |
| 5,459,257 | 10/1995 | Shoji et al. | 536/118 |
| 5,489,578 | 2/1996 | Rosen et al. | 514/261 |
| 5,498,602 | 3/1996 | Shoji et al. | 514/25 |
| 5,760,015 | 6/1998 | Joullié et al. | 514/58 |
| 5,846,954 | 12/1998 | Joulliéet al. | 514/58 |

OTHER PUBLICATIONS

Croft et al., "Synthesis of Chemically Modified Cyclodextrins," (Tetrahedron Report No. 147), *Tetrahedron*, 39(9), 1417–1474 (1983).

*Primary Examiner*—L. Eric Crane
*Attorney, Agent, or Firm*—Pennie & Edmonds LLP

[57] ABSTRACT

A cyclic oligosaccharide or salts thereof comprising glucoses bound cyclically via $\alpha$-1,6-linkages and having at least one S-oxo acid group bound, and ana gent for preventing or treating retroviral diseases which comprises said cyclic oligosaccharide or salts thereof as an active ingredient. The novel sulfated cyclic isomaltoligosaccharide inhibits infection of host cells with various retroviruses such as AIDS virus etc. so effectively that it has a significant preventive and therapeutic effect on diseases caused by retroviruses. Accordingly, said oligosaccharide can be utilized as an agent for preventing or treating retroviral diseases in pharmaceutical industry.

25 Claims, 5 Drawing Sheets

CYCLIC OLIGOSACCHARIDE, AND AN AGENT CONTAINING THE SAME FOR PREVENTING OR TREATING RETROVIRAL DISEASES

FIELD OF THE INVENTION

The present invention relates to a novel cyclic oligosaccharide and an agent containing the same for preventing or treating retroviral diseases.

BACKGROUND OF THE INVENTION

The cyclic isomaltoligosaccharide is a cyclic oligosaccharide with 7 to 9 glucoses bound cyclically via α-1,6-linkages. The cyclic isomaltoligosaccharide has a hollow space in the molecule, and the inside of this hollow space, as similar to cyclic dextrin (hereinafter abbreviated as CD), is hydrophobic and thus has an inclusion action for incorporating various oily substances into it. Because of this action, application of the cyclic isomaltoligosaccharide is expected in the fields of food industry, chemical industry, pharmaceutical industry etc. Further, unlike CD, the cyclic isomaltoligosaccharide specifically inhibits the action of glucan synthase produced by cariogenic bacteria. As a result, formation of dental plaques as a cause for dental caries is significantly prevented, so application thereof as cariostatic agent is also expected.

Heretofore, nucleic acid analogues such as azidothymidine (AZT), dideoxyinosine (DDI) etc. which are inhibitors for reverse transcriptases transcribing retroviral RNA into DNA, as well as protease inhibitors derived from retroviruses, have been utilized for the purpose of preventing and treating retroviral diseases, particularly AIDS. However, nucleic acid analogs such as AZT etc., if administered for a long period of time, cause disorders in bone marrow or side effects such as acute pancreatitis and peripheral neuropathy or lead to generation of viruses resistant to these drugs. The protease inhibitors also suffer from the problem of generation of resistant viruses upon long-term administration. Therefore, treatment of AIDS etc. at present makes use of a combination of drugs each having different working mechanism, but there is nevertheless the problems of side effects upon long-term administration or the possibility of generation of new resistant viruses.

Meanwhile, in 1987, it was revealed that sulfated polysaccharides represented by dextran sulfate significantly inhibit the binding of AIDS virus to the CD4 receptor on the surface of T cells in a completely different mode of action to those of the above-described drugs. These sulfated polysaccharides are extremely low in cytotoxicity and inexpensive so their practical application was expected. However, these sulfated polysaccharides exhibited significant inhibitory activity in vitro but did not in vivo. The presumed reason is that they are hardly absorbed because of their high molecular weight or that the polysaccharides are subject to decomposition in a living body. A sulfated CD derivative appeared to compensate for this drawback. However, although this substance is absorbed relatively easily into a living body, there may be a problem with the strong hemolytic activity inherent in CD, so it is still not practical for use even now.

SUMMARY OF THE INVENTION

The object of the present invention is to provide a novel cyclic oligosaccharide and an agent containing the same for preventing or treating retroviral diseases.

Under these circumstances, the present inventors extensively studied a cyclic isomaltoligosaccharide, and as a result, they found that a novel derivative, a sulfated cyclic isomaltoligosaccharide, inhibits the binding of AIDS (acquired immune deficiency syndrome) virus gp120 to the CD4 receptor on T cells, and on the basis of this finding, the present invention was completed.

That is, the present invention relates to a cyclic oligosaccharide or salts thereof comprising glucoses bound cyclically via 1,6-linkages and having at least one S-oxo acid group bound thereto. The cyclic oligosaccharide consists of 7 to 9 glucoses.

Further, the present invention relates to a sulfated cyclic isomaltooctaose represented by the general formula (I):

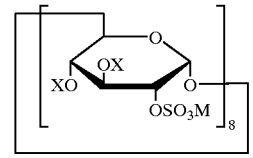

wherein X is $SO_3M$ (M is a hydrogen atom, an alkali metal, an alkaline earth metal, ammonia or an organic amine) or H, and X in each constituent sugar may be the same or different, the total number of X that is $SO_3M$ is 7 to 11, and M has the same meaning as above, as well as salts thereof; a sulfated cyclic isomaltoheptaose represented by the general formula (II):

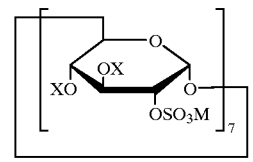

wherein X is $SO_3M$ (M is a hydrogen atom, an alkali metal, an alkaline earth metal, ammonia or an organic amine) or H, and X in each constituent sugar may be the same or different, the total number of X that is $SO_3M$ is 6 to 10, and M has the same meaning as above, as well as salts thereof; and a sulfated cyclic isomaltononaose represented by the general formula (III):

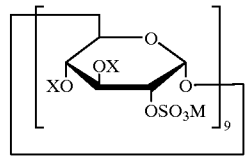

wherein X is $SO_3M$ (M is a hydrogen atom, an alkali metal, an alkaline earth metal, ammonia or an organic amine) or H, and X in each constituent sugar may be the same or different, the total number of X that is $SO_3M$ is 8 to 12, and M has the same meaning as above, as well as salts thereof.

Further, the present invention relates to a cyclic isomaltooctaose heptadecasulfate salt wherein the total number of X that is $SO_3M$ in the general formula (I) is 9, and M is Na or $NH_4$.

Further, the present invention relates to an S-oxo acid group-containing oligosaccharide obtained by reacting a cyclic isomaltoligosaccharide with S-oxo acid, as well as salts thereof. The cyclic isomaltoligosaccharide is derived from a microorganism or obtained by chemical synthesis.

The above-described cyclic oligosaccharide includes a sulfated cyclic isomaltoligosaccharide, and said sulfated cyclic isomaltoligosaccharide has a molecular weight of 400 to 4,000, preferably 1,400 to 3,800, and has a sulfur content of 2 to 25%, preferably 5 to 24%, more preferably 15 to 20%.

Further, the present invention relates to an agent for preventing or treating retroviral diseases which comprises said oligosaccharide or salts thereof as an active ingredient. The retroviral diseases include PGL (progressive general lymphoma) LAS (lymphadenopathy syndrome), ARC (AIDS-related complex), AIDS (acquired immuno deficiency syndrome), adult T cell leukemia or Kawasaki's disease.

The above-described retrovirus include a human retrovirus. The human retrovirus includes e.g. HTLV-III (human T cell leukemia virus III type), HIV such as LAV and ARV, HTLV-I (human T cell leukemia virus I type), HTLV-II (human T cell leukemia virus II type) or Kawasaki's disease virus. The above-described retrovirus also includes a non-human animal retrovirus, which includes e.g. bird myeloblast cis-virus or Friend leukemia virus.

DETAILED DESCRIPTION OF THE INVENTION

Figure 1:
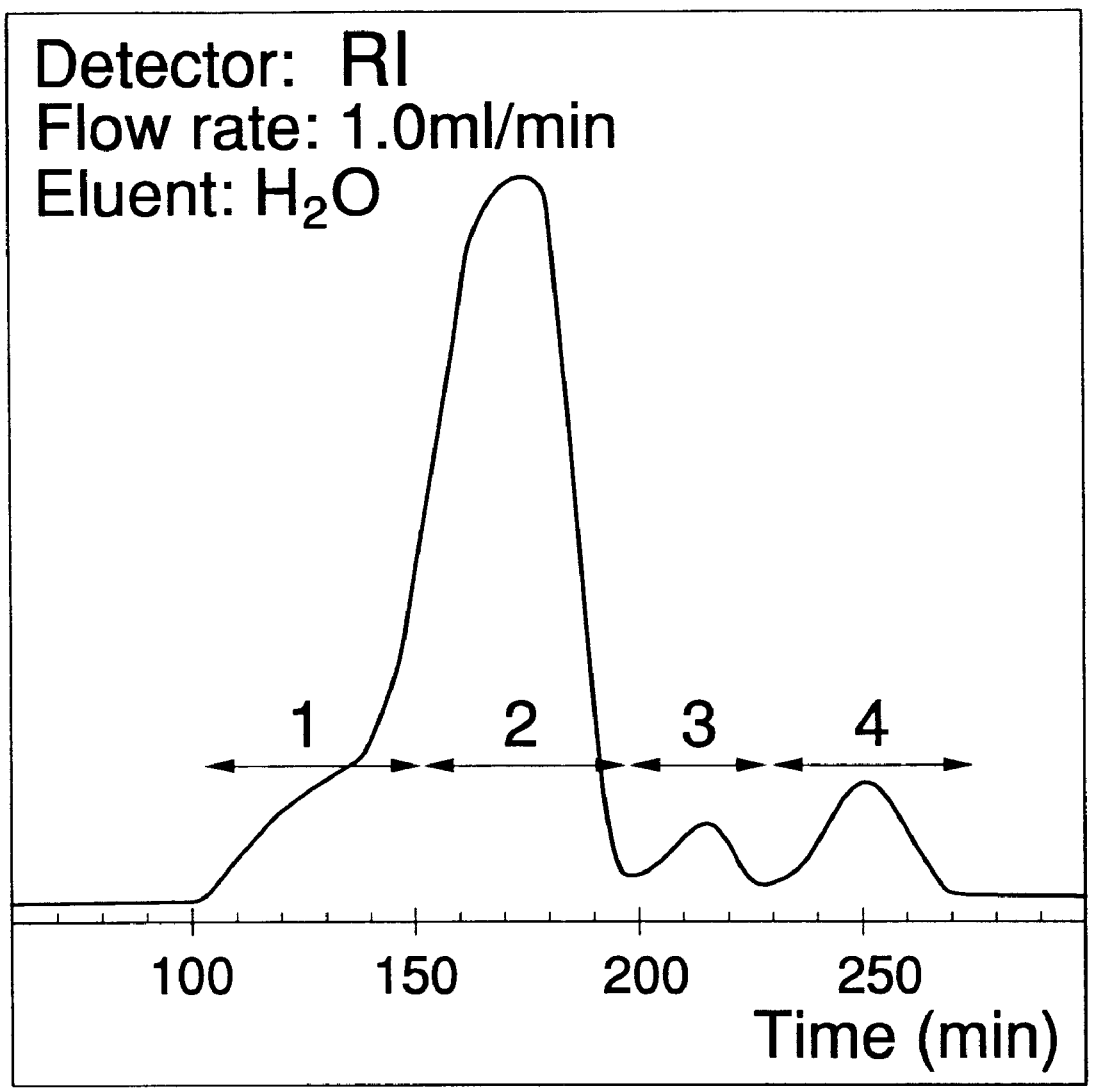
FIG. 1 shows an elution curve of the reaction product in Example 1 through a Sephadex LH-20 column.

Hereinafter, the present invention is described in detail.

The sulfated cyclic isomaltooctaose of formula (I) in the present invention or salts thereof, the sulfated cyclic isomaltoheptaose of formula (II) or salts thereof, and the sulfated cyclic isomaltononaose of formula (III) or salts thereof can be obtained in any methods, for example by sulfating cyclic isomaltoctaose, cyclic isomaltoheptaose or cyclic isomaltononaose (hereinafter, these 3 types of oligosaccharide are abbreviated to cyclic isomaltoligosaccharide), followed by converting it into a salt.

The cyclic isomaltoligosaccharide as the starting material is a known substance and is represented by the general formula (IV):

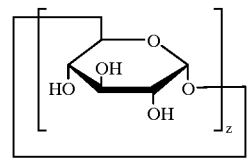

(IV)

wherein z is 7 to 9. The compound of formula (IV) is cyclic isomaltoctaose if z is 8, cyclic isomaltoheptaose if z is 7, and cyclic isomaltononaose if z is 9. These cyclic isomaltoligosaccharides can be obtained by allowing cyclic isomaltoligosaccharide synthase or a microorganism (e.g. Bacillus sp. T-3040 (FERM BP-4132)) belonging to the genus Bacillus and having the ability to produce said cyclic isomaltoligosaccharide synthase to act on commercial dextran (see Japanese Laid-Open Patent Publication No. 8276/1995).

The agent used for sulfating the cyclic isomaltoligosaccharide in the present invention includes e.g. a pyridine-$SO_3$ complex, a trimethylamine-$SO_3$ complex, piperidine sulfuric acid, chlorosulfonic acid, sulfuric anhydride, conc. sulfuric acid etc.

These are used for sulfating the cyclic isomaltoligosaccharide, where any method can be used. Usually, the cyclic isomaltoligosaccharide is dissolved in 20 to 200-fold excess amount (ratio by weight) of N,N-dimethylformamide (DMF) or dimethylsulfoxide (DMSO), and the sulfating agent is added in an amount of 3 to 100-fold molar excess, preferably 20 to 50-fold molar excess relative to the cyclic isomaltoligosaccharide and the mixture is reacted at 50 to 120° C. and preferably 60 to 80° C. to prevent side reactions. Depending on the type of the sulfating agent, the temperature, solvent, concentration etc., the reaction time is usually 2 to 24 hours.

A conventional method is used for purification of the resulting product, and for example column chromatography can be used using a gel column or a silica gel column such as Sephadex LH-20, Toyopearl HW-20 etc. As necessary, strong cation-exchange resin AG50W, Dowex 50W, or Amberlite IR-120 can be used to make the sulfate group free (—$OSO_3H$ form), and further a desired base such as NaOH, KOH, ammonia water, triethylamine or the like is added to the free sulfate so that it can be converted into a sulfate salt thereof.

Examples of sulfated cyclic isomaltoligosaccharides represented by the general formulae (I), (II) and (III), or salts thereof, are cyclic isomaltoctaose $2^1, 3^1, 2^2, 3^2, 2^3, 3^3, 2^4, 3^4, 2^5, 3^5, 2^6, 3^6, 2^7, 3^7, 2^8, 3^8, 4^8$-heptadeca-0-sulfate, cyclic isomaltoctaose $2^1, 3^1, 2^2, 3^2, 2^3, 3^3, 2^4, 3^4, 2^5, 3^5, 2^6, 3^6, 2^7, 3^7, 2^8, 3^8$-hexadeca-0-sulfate sodium salt, cyclic isomaltoctaose-$2^1, 3^1, 2^2, 3^2, 2^3, 3^3, 2^4, 3^4, 2^5, 3^5, 2^6, 3^6, 2^7, 3^7, 2^8, 3^8, 4^8$-nonadeca-0-sulfate potassium salt, cyclic isomaltoctaose-$2^1, 2^2, 3^2, 2^3, 3^3, 2^4, 3^4, 2^5, 3^5, 2^6, 3^6, 2^7, 3^7, 2^8, 3^8$-pentadeca-0-sulfate ammonium salt, cyclic isomaltoctaose-$2^1, 3^1, 2^2, 3^2, 2^3, 3^3, 4^3, 2^4, 2^5, 3^5, 4^5, 2^6, 3^6, 2^7, 3^7, 2^8, 3^8, 4^8$-octadeca-0-sulfate triethylamine salt, cyclic isomaltoheptaose $2^1, 3^1, 2^2, 3^2, 2^3, 3^3, 2^4, 3^4, 2^5, 3^5, 2^6, 3^6, 2^7, 3^7, 4^7$-pentadeca-0-sulfate, cyclic isomaltoheptaose $2^1, 3^1, 2^2, 3^2, 2^3, 3^3, 2^4, 3^4, 2^5, 3^5, 2^6, 3^6, 2^7, 3^7$-tetradeca-0-sulfate alminum salt, cyclic isomaltoheptaose-$2^1, 3^1, 2^2, 3^2, 4^2, 2^3, 3^3, 2^4, 3^4, 2^5, 3^5, 4^5, 2^6, 3^6, 2^7, 3^7, 4^7$-heptadeca-0-sulfate calcium salt, cyclic isomaltoheptaose-$2^1, 2^2, 3^2, 2^3, 3^3, 2^4, 3^4, 2^5, 3^5, 2^6, 3^6, 2^7, 3^7$-trideca-0-sulfate potassium salt, cyclic isomaltoheptaose-$2^1, 3^1, 2^2, 3^2, 2^3, 3^3, 4^3, 2^4, 2^5, 3^5, 4^5, 2^6, 3^6, 2^7, 3^7, 4^7$-hexadeca-0-sulfate trimethylamine salt, cyclic isomaltononaose $2^1, 3^1, 2^2, 3^2, 2^3, 3^3, 2^4, 3^4, 2^5,$ $3^5, 2^6, 3^6, 2^7, 3^7, 2^8, 3^8, 2^9, 3^9, 4^9$-nonadeca-0-sulfate, cyclic isomaltononaose $2^1, 3^1, 2^2, 3^2, 2^3, 3^3, 2^4, 3^4, 2^5, 3^5, 2^6, 3^6, 2^7, 3^7, 2^8, 3^8, 2^9, 3^9$-octadeca-0-sulfate ammonium salt, cyclic isomaltoctaose-$2^1, 3^1, 2^2, 3^2, 4^2, 2^3, 3^3, 2^4, 3^4, 3^5, 4^5, 2^6, 3^6, 2^7, 3^7, 2^8, 3^8, 4^8, 2^9, 3^9$-heneicosa-0-sulfate sodium salt etc. Each upper right small number assigned to each number is given to distinguish each of contiguous glucose residues in the cyclic isomaltoligosaccharide.

Diseases which can be prevented or treated by the sulfated cyclic isomaltoligosaccharides obtained in the present invention may be any retroviral diseases including AIDS, ARC, PGL and LAS, and the onset of symptom-free AIDS can be prevented as well.

Their administration may be conducted using any arbitrary method such as oral, anal, nasal, topical (e.g. sublingual) vaginal administration, by injection (subcutaneous, intramuscular, intravenous, intracutaneous) administration or by application etc. Further, the active ingredient can be mixed with organic or inorganic solid or liquid fillers suitable for said administration method so that it can be administered in the form of customary pharmaceutical preparations. Such preparations can contain e.g. solids such as tablets, granules, powder, capsules etc., liquids such as liquid agents, emulsifiers, suspending agents etc., as well as ointments.

The dose of the active ingredient is not limited insofar as it is in an amount enough to bring about the desired therapeutic effect. For example, the active ingredient is administered in an amount of 0.1 to 800 mg/kg, preferably 0.4 to 300 mg/kg in one or divided portions a day or as a sustained releasing preparation to attain blood levels for bringing about the anti-viral activity.

<Reference Example 1>

Production of cyclic isomaltooctaose (abbreviated hereinafter to CI-8)

100 ml liquid medium (using tap water, pH 7.0) consisting of 1% dextran 40 (Meito Sangyo K. K.), 1% peptone (Kyokuto Seiyaku K. K.), 0.5% NaCl and 0.1% yeast extract (Difco) was introduced into a 500-ml flask and sterilized at 120° C. for 20 minutes, and from a storage slant of Bacillus sp. T-3040 strain (FERMBP-4132), the microorganism was inoculated via a platinum loop into the medium and cultured at 30° C. for 1 day under shaking to give a culture.

1000 ml of this culture was inoculated into a 500-L tank containing 300 L medium having the same composition and sterilized under the same condition as above. The microorganism was cultured in it for 3 days under aeration at 30° C., 0.25 vvm and 70 rpm. After culture was finished, the microorganism was removed from 300 L of the culture through Microsa® (ultrafiltration membrane, a product of Asahi Chemical Industry Co., Ltd.), the resulting filtrate was concentrated to 6.3 L through a hollow fiber (cut off molecular weight: 6000), and the concentrate, 900 ml per tube, was frozen and stored at −20° C.

A part of this concentrate was mixed with an aqueous solution of 100 g dextran (Meito Sangyo K. K.) in 10 L of 10 mM phosphate buffer, pH 6.5, and incubated at 40° C. for 48 hours. Activated charcoal was added to it and the mixture was boiled so that the reaction was terminated and simultaneously the unreacted dextran was adsorbed. The supernatant from which the activated charcoal was removed was applied to a column of activated charcoal previously equilibrated with de-ionized water, the column was washed with de-ionized water, and the adsorbed oligosaccharide was eluted with an ethanol concentration gradient. The cyclic oligosaccharide fractions were collected, concentrated, applied to an ODS column equilibrated with de-ionized water. The column was washed with de-ionized water. Then the oligosaccharide was eluted with an ethanol concentration gradient and each cyclic isomaltoligosaccharide fraction was collected to give 4.6 g of CI-8. Simultaneously, 2.1 g of cyclic isomaltoheptaose and 1.0 g of cyclic isomaltononaose were obtained as other cyclic isomaltoligosaccharide components (see Japanese Laid-Open Patent Publication No. 8276/1995).

According to the present invention, the novel sulfated cyclic isomaltoligosaccharide inhibits infection of host cells with various retroviruses such as AIDS virus etc. so effectively that it is considered to have a significant preventive and therapeutic effect on diseases caused by retroviruses. Accordingly, said oligosaccharide can be utilized as an agent for preventing or treating retroviral diseases in pharmaceutical industry.

EXAMPLES

Hereinafter, the formation and application of said oligosaccharide are described with reference to Examples which however are not intended to limit the present invention.

[Example 1]

Synthesis of cyclic isomaltoctaose-heptadecyl-0-sulfate sodium salt 1.037 g (0.800 mmol) cyclic isomaltoctaose was dissolved in 40 ml DMF, and 4.0 g (0.029 mol) trimethylamine $SO_3$ complex was added, and the mixture was reacted at 70° C. for 24 hours under vigorous stirring. After it was confirmed that a viscous brown solid reaction product was formed, the DMF was removed by decantation. The reaction product was dissolved by adding 6% (w/v) sodium acetate (about 200 ml) to it, and the pH of the solution was adjusted to 7.0. 500 ml ethanol was added to this solution, and the resulting precipitates were collected on a glass filter, then dissolved in water and lyophilized. 2 g of the resulting lyophilized sample was dissolved in 40 ml water to give 5% (w/v) solution.

This solution was applied to column chromatography on Sephadex LH-20 (ø25 mm×720 mm) and eluted with water as an eluent at a flow rate of 1.0 ml/min. A profile of this elution is shown in FIG. 1. The fractions arrowed in FIG. 1 were collected and lyophilized to give 1.7 g cyclic isomaltoctaose-heptadecyl-0-sulfate sodium salt.

[Example 2]

Synthesis of cyclic isomaltoheptaose-pentadecyl-0-sulfate sodium salt 1.026 g (0.900 mmol) cyclic isomaltoheptaose was dissolved in 40 ml DMF, and 4.0 g (0.025 mol) pyridine $SO_3$ complex was added, and the mixture was reacted at 70° C. for 6 hours under vigorous stirring. After it was confirmed that a viscous brown solid reaction product was formed, the DMF was removed by decantation. The reaction product was dissolved in 10 ml water, applied to column chromatography on Dowex 50W-X8 ($H^+$ type) (ø30 mm×200 mm) and eluted with water. The eluate was collected, adjusted to pH 7.0 with 0.2 N sodium hydroxide, and concentrated under reduced pressure to give about 10 ml of 20% (w/v) solution.

This concentrate was subjected to column chromatography on TOYOPEARL HW-40 (Tosoh) (ø50 mm×450 mm)

and eluted with water as an eluent at a flow rate of 1.0 ml/min. The eluate, 15 ml per fraction, was collected and analyzed by TLC (silica gel plate, developer; n-propanol:ethyl acetate:water=7:3:6 v/v/v) and HPLC (TSK gel G3000SW$_{XL}$ ø7.8 mm×300 mm×2, eluent; 0.2 M sodium nitrate). The objective fractions were collected, decolorized with activated charcoal, concentrated under reduced pressure and lyophilized to give 1.6 g cyclic isomaltoheptaose-pentadecyl-0-sulfate sodium salt.

[Example 3]

Synthesis of cyclic isomaltononaose-nonadecyl-0-sulfate sodium salt 1.7 g cyclic isomaltononaose-nonadecyl-0-sulfate sodium salt was obtained in the same manner as in Example 1 except that 1.021 g (0.700 mmol) cyclic isomaltononaose was used as the starting material.

[Example 4]

Synthesis of cyclic isomaltomaltooctaose-heptadecyl-0-sulfate ammonium salt 5 g sulfated cyclic isomaltooctaose sodium salt synthesized in the same manner as in Example 1 was dissolved in 100 ml water, subjected to column chromatography on Dowex 50W-X8 (H$^+$ type) (ø30 mm×200 mm), and eluted with water. The eluate was collected and adjusted to pH 8.5 with ammonia water. It was concentrated under reduced pressure to give about 20 ml of 20% solution.

This concentrate was subjected to column chromatography on Sephadex LH-20 (ø50 mm×450 mm) and eluted with water as an eluent at a flow rate of 1.0 ml/min. The eluate, 15 ml per fraction, was collected and analyzed by TLC (silica gel plate, developer; n-propanol:ethyl acetate:water= 7:3:6) and HPLC (TSK gel G3000SW$_{XL}$ ø7.8 mm×300 mm×2, eluent; 0.2 M sodium nitrate). The objective fractions were collected, decolorized with activated charcoal, concentrated under reduced pressure and lyophilized to give 3.5 g cyclic isomaltooctaose-heptadecyl-0-sulfate ammonium salt.

Elementary analysis: Determined as $C_{48}H_{131}N_{17}O_{91}S_{17}$ 13H$_2$O

|  | C | H | N | S |
|---|---|---|---|---|
| Theoretical (%) | 18.12 | 4.97 | 7.48 | 17.13 |
| Found (%) | 18.13 | 4.80 | 7.52 | 16.93 |

[Example 5]

Synthesis of cyclic isomaltoheptaose-pentadecyl-0-sulfate ammonium salt 0.7 g cyclic isomaltoheptaose-pentadecyl-0-sulfate ammonium salt was obtained in the same manner as in Example 4 except that 1 g cyclic isomaltoheptaose-pentadecyl-0-sulfate sodium salt synthesized in the same manner as in Example 2 was used. Elementary analysis: Determined as $C_{42}H_{115}N_{15}O_{80}S_{15}$ 12H$_2$O

|  | C | H | N | S |
|---|---|---|---|---|
| Theoretical (%) | 17.97 | 4.99 | 7.48 | 17.13 |
| Found (%) | 18.08 | 4.82 | 7.48 | 16.92 |

[Example 6]

Synthesis of cyclic isomaltononaose-nonadecyl-0-sulfate ammonium salt 1.2 g cyclic isomaltononaose-nonadecyl-0-sulfate ammonium salt was obtained in the same manner as in Example 4 except that 2 g cyclic isomaltononaose-nonadecyl-0-sulfate sodium salt synthesized in the same manner as in Example 3 was used. Elementary analysis: Determined as $C_{54}H_{147}N_{19}O_{102}S_{19}$ 15H$_2$O

|  | C | H | N | S |
|---|---|---|---|---|
| Theoretical (%) | 18.15 | 4.99 | 7.45 | 17.04 |
| Found (%) | 18.21 | 4.92 | 7.39 | 17.14 |

[Example 7]

Quantification of sulfate ions by ion chromatography 10 mg of sulfated CI-8 sodium prepared in Example 1 was dissolved in 0.2 N aqueous hydrochloric acid, sealed and acid-hydrolyzed at 95° C. for 16 hours. The resulting hydrolysate was immediately analyzed for its free sulfate ions by ion chromatography. As a result, it was found that 15 to 20 sulfate groups were contained in 1 molecule of sulfated CI-8.

<Reference Example 2>

Methylation analysis of cyclic isomaltooctaose-heptadecyl-0-sulfate ammonium salt 3.0 g completely dried cyclic isomaltooctaose-heptadecyl-0-sulfate ammonium salt was dissolved in 600 ml DMSO, and 9 g of sodium hydride, from which a mineral oil was previously removed with pentane, and 150 ml methyl iodide (MeI), were added thereto, and the mixture was reacted at 45° C. for 5 hours. After the reaction was terminated, the DMSO was distilled off under reduced pressure, and the resulting residue was dissolved in 500 ml water. It was washed with chloroform (200 ml×3). Then, 500 ml strongly acidic ion-exchange resin Dowex 50W-8 (H$^+$ type) was added to the aqueous layer, and the mixture was stirred for 18 hours, and the resin was separated by a glass filter and washed with 500 ml water. The filtrate and the washing were combined and concentrated under reduced pressure to give 200 ml concentrate which was then decomposed by heating it at 100° C. for 2 days. After the reaction was finished, the reaction solution was washed with chloroform (200 ml×3), and the aqueous layer was concentrated under reduced pressure to give 45 ml of 20% (w/v) solution.

This solution was applied to column chromatography on Sephadex LH-20 (ø60 mm×500 mm) and eluted with water as an eluent at a flow rate of 1.0 ml/min. The eluate, 15 ml per fraction, was collected and analyzed by TLC (silica gel plate, developer; ethyl acetate:methanol:water=8:2:0.1 v/v/v), and fractions containing the methylated saccharide were concentrated to give 2.7 g residue. This residue was subjected to silica gel chromatography (ø30 mm×400 mm), and the objective fractions (F1, F2 and F3) eluted with ethyl acetate:methanol:water=8:2:0.2 (v/v/v) were dried under reduced pressure respectively, whereby 28 mg of 3,4-di-0-methyl glucose was obtained from the F1 fraction, 184 mg of 3-0-methyl glucose from the F2 fraction, and 166 mg of 4-0-methyl glucose from the F3 fraction. 2-0-methyl glucose and tri-0-methyl glucose were not contained in the chloroform layer used in washing the aqueous water and in said washing.

From the foregoing, it was strongly suggested that sulfate groups were introduced equally into OH groups at either the 3-or 4-position in each of almost all glucose residues or rarely into OH groups at both the 3- and 4-positions in each glucose residue in the cyclic isomaltooctaose-heptadecyl-0-sulfate ammonium salt, and also that a sulfate group was always introduced into an OH group at the 2-position.

<Reference Example 3>

Sulfonation of methyl 6-chloro-6-deoxy-α-D-glucoside

Commercially available methyl 6-chloro-6-deoxy-α-D-glucoside, 1.06 g, was dissolved in 60 ml DMF, then 3.13 g trimethylamine-$SO_3$ complex was added thereto, and the mixture was reacted at 70° C. for 20 hours under stirring. Then, the DMF was distilled off under reduced pressure, the resulting residue was subjected to silica column chromatography, and objective fractions (F1, F2 and F3) eluted with ethyl acetate:methanol:water=8:2:0.5 (v/v/v) were dried under reduced pressure, treated with strongly acidic ion-exchange resin AG50W-8 and neutralized with 28% ammonia water.

Figure 2:
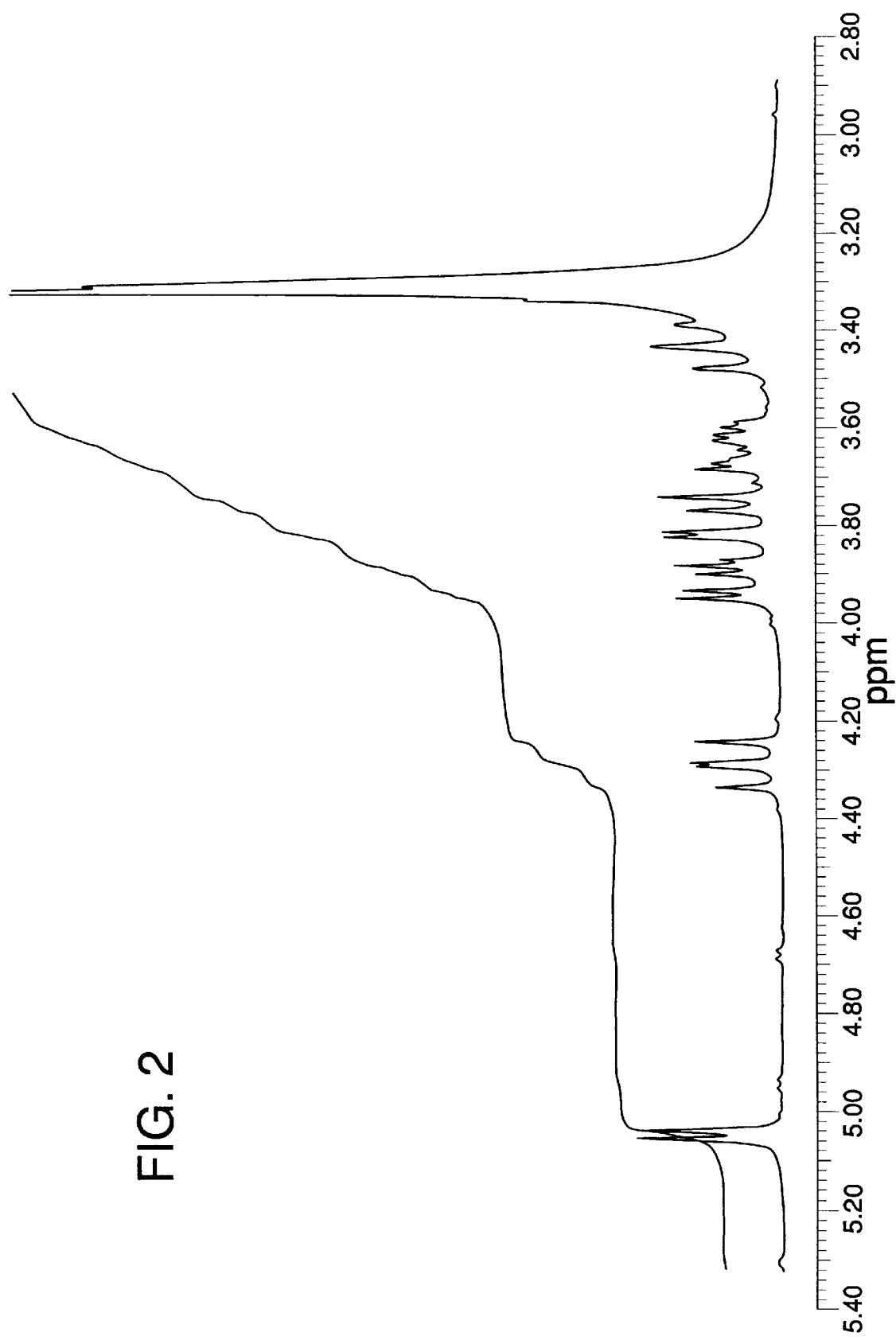
FIG. 2 shows a profile in NMR analysis of methyl 6-chloro-6-deoxy-α-D-glucoside-2,3-di-0-sulfate ammonium salt in F1 fraction.
Figure 3:
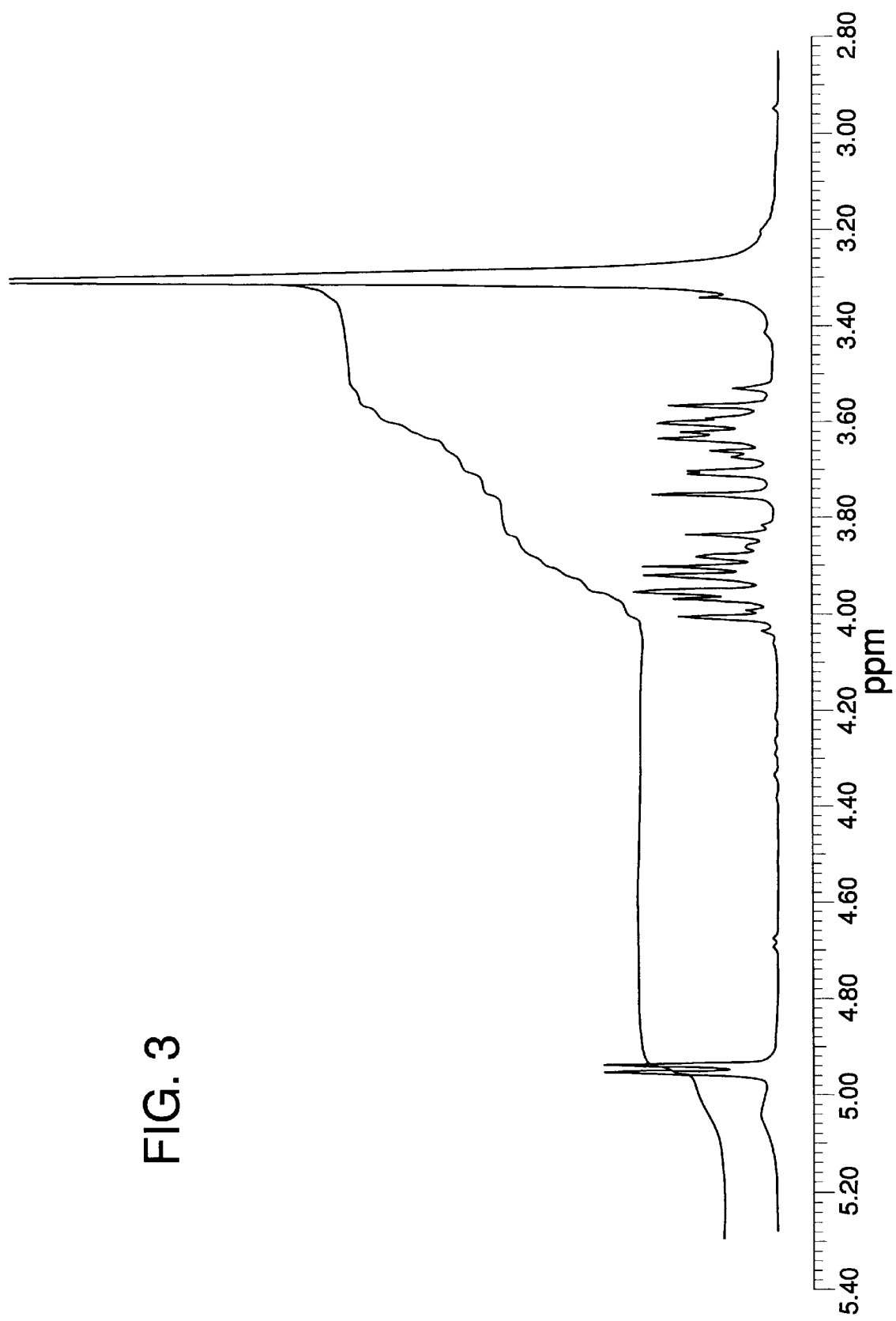
FIG. 3 shows a profile in NMR analysis of methyl 6-chloro-6-deoxy-α-D-glucoside-2,4-di-0-sulfate ammonium salt in F2 fraction.
Figure 4:
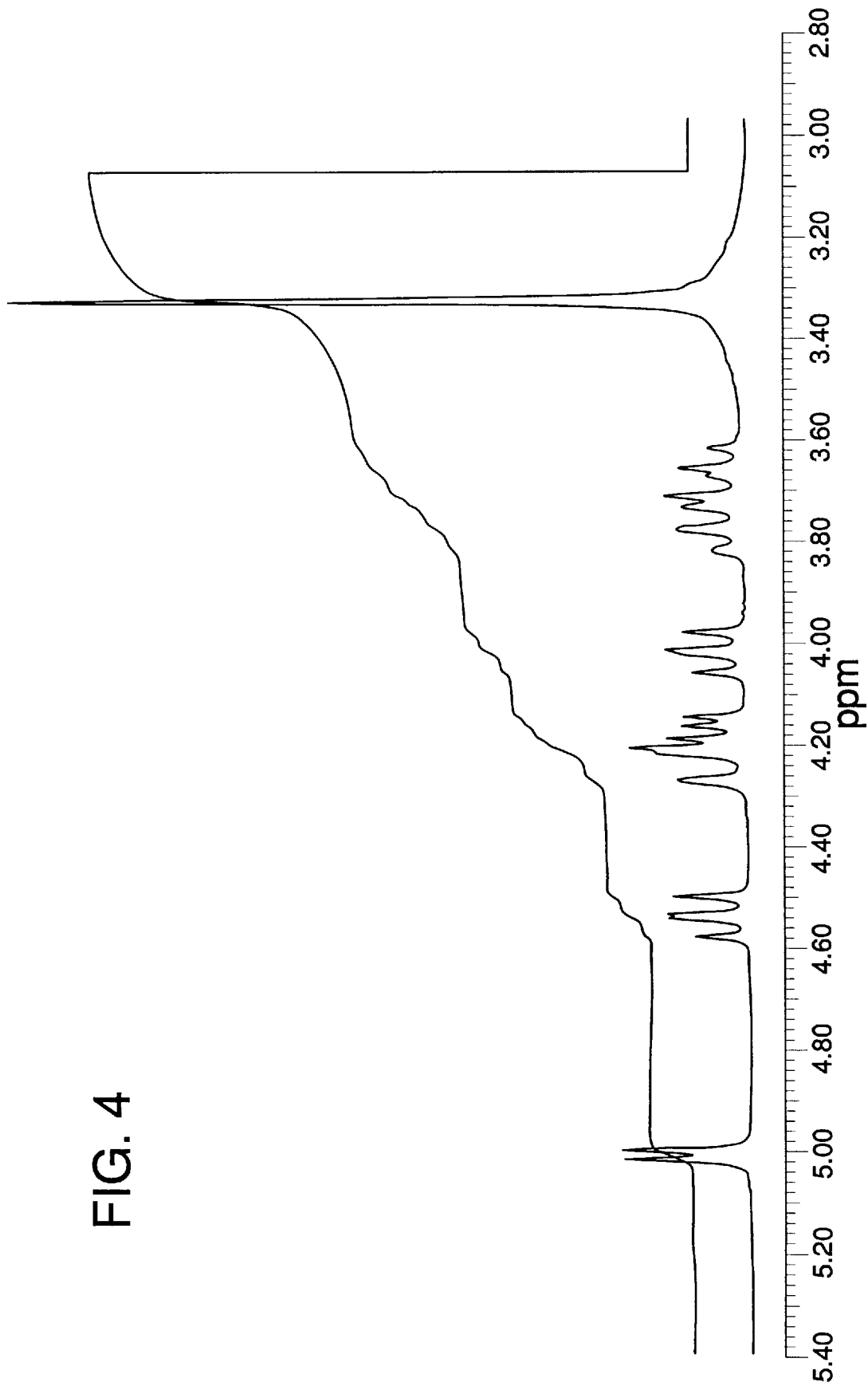
FIG. 4 shows a profile in NMR analysis of methyl 6-chloro-6-deoxy-α-D-glucoside-2,3,4-tri-0-sulfate ammonium salt in F3 fraction.

The 3 fractions were applied to a Sephadex LH-20 column respectively, the desired fractions eluted with water were lyophilized whereby 613 mg of methyl 6-chloro-6-deoxy-α-D-glucoside-2,3-di-0-sulfate ammonium salt was obtained from the F1 fraction, 468 mg of methyl 6-chloro-6-deoxy-α-D-glucoside-2,4-di-0-sulfate ammonium salt from the F2 fraction, and 550 mg of methyl 6-chloro-6-deoxy-α-D-glucoside-2,3,4-tri-0-sulfate ammonium salt from the F3 fraction. Their NMR charts are shown in FIGS. 2 to 4 respectively.

From the foregoing, it was found that upon sulfation of glucose residues with OH groups at the α 1- and 6-positions substituted, sulfation of an OH-group at the 2-position is always sulfated, an OH group is sulfated with similar probability at either the 3- or 4-position, and OH groups at both the 3- and 4-positions are rarely sulfated. From this, it was strongly suggested that upon sulfation of the cyclic isomaltoligosaccharide under the same conditions, sulfate groups are introduced into every OH group at the 2-position, into an OH group at either the 3- or 4-position equally, and rarely into OH groups at both the 3- and 4-positions in each of 1,6-0-di-substituted glucose residues.

[Example 8]

Measurement of anti-HIV activity of sulfated CI-8

Figure 5:
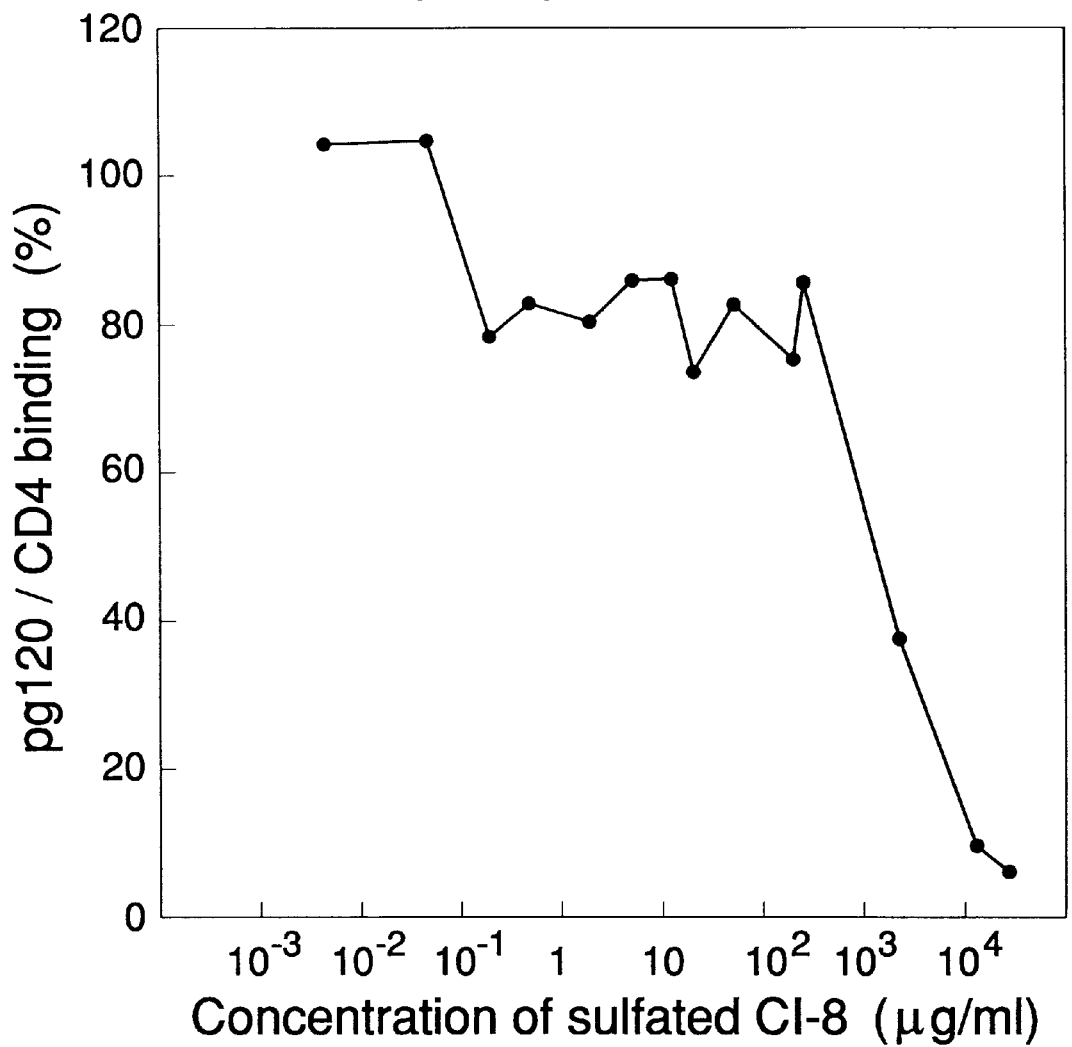
FIG. 5 shows the inhibitory activity of sulfated CI-8 on the binding of gp120 to CD4 receptor.

Sulfated CI-8 obtained above in Example 1 was examined for the activity of inhibiting the binding of gp120 to CD4 receptor in the concentration range of 0 to 100 mg/ml using a drug discovery kit (duPont). As shown in FIG. 5, sulfated CI-8 inhibited the binding of pg120 to CD4 in proportion to its concentration.

[Example 9]

Anticoagulation activity of sulfated cyclic oligosaccharide

Sulfated CI-8 was examined for its anticoagulation activity. 1% aqueous sulfated CI-8 solution obtained by dissolving 10 mg of sulfated CI-8 sodium in 1 ml de-ionized water was diluted at various concentrations with 0.85% sterilized NaCl solution (physiological saline) to prepare sulfated CI-8 solutions at various concentrations. Solutions of dextran 5000 sodium sulfate (Wako Pure Chemical Industries, Ltd.) at various concentrations were also prepared in the same manner. Standard solutions at various concentrations were prepared using dextran sodium sulfate having 20 U/mg anticoagulation activity (a gift from Meito Sangyo K. K.).

40 µl each of the aqueous solutions were put to each well on a 96-well microtiter plate. Then, 50 µof fresh rat blood containing 0.38% trisodium citrate was put to each well and mixed. Further, 10 µl of 2% aqueous $CaCl_2$ solution and mixed whereby blood-coagulation reaction was initiated. The plate was left at room temperature for 15 minutes and centrifuged at 2000 rpm for 10 minutes, and the separation of the serum in each well was visually evaluated. As a result, the anticoagulation activity of sulfated CI-8 was judged to be about ½ relative to the known dextran sodium sulfate, so its activity was judged to be about 10 U/ml. The activity of dextran 5000 sodium sulfate was judged to be about 40 U/mg.

What is claimed is:

1. A cyclic oligosaccharide or salts thereof formed of glucoses bound cyclically via α-1,6-linkages and having at least one S-oxo acid group bound thereto.

2. The cyclic oligosaccharide or salts thereof according to claim 1 having 7 to 9 glucoses.

3. The cyclic oligosaccharide or salts thereof according to claim 1 obtained by contacting a cyclic oligosaccharide with a sulfating agent.

4. The method of claim 3 wherein the sulfating agent is an S-oxo acid.

5. The method of claim 3 wherein the sulfating agent is a sulfur trioxide adduct.

6. The cyclic oligosaccharide or salts thereof according to claim 1, 2, or 3 wherein the cyclic oligosaccharide is derived from a microorganism or obtained by chemical synthesis.

7. A pharmaceutical composition comprising the oligosaccharide or salts thereof of claim 6 as an active ingredient.

8. A cyclic oligosaccharide or salts thereof of claim 1 or 3, wherein the cyclic oligosaccharide is a sulfated cyclic isomaltoligosaccharide.

9. The cyclic oligosaccharide or salts thereof according to claim 8 wherein the sulfated cyclic isomaltoligosaccharide has a molecular weight of 400 to 4,000.

10. The cyclic oligosaccharide or salts thereof according to claim 8 wherein the sulfated cyclic isomaltoligosaccharide has a sulfur content of 2 to 25%.

11. The compound according to claim 8 wherein the sulfated cyclic isomaltoligosaccharide has a molecular weight of 1,400 to 3,800.

12. The compound according to claim 8 wherein the sulfated cyclic isomaltoligosaccharide has a sulfur content of 5 to 24%.

13. The compound according to claim 8 wherein the sulfated cyclic isomaltoligosaccharide has a sulfur content of 15 to 20%.

14. A pharmaceutical composition comprising the oligosaccharide or salts thereof of claim 8 as an active ingredient.

15. A sulfated cyclic isomaltooctaose or salts thereof represented by the general formula (I):

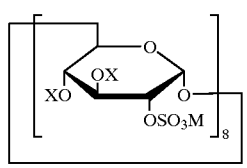

(I)

wherein X is SO$_3$M (M is a hydrogen atom, an alkali metal, an alkaline earth metal, ammonia or an organic amine) or H, and X in each constituent sugar may be the same or different, the total number of X that is SO$_3$M is 7 to 11, and M has the same meaning as above.

16. A sulfated cyclic isomaltoheptaose or salts thereof represented by the general formula (II):

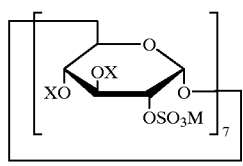

(II)

wherein X is SO$_3$M (M is a hydrogen atom, an alkali metal, an alkaline earth metal, ammonia or an organic amine) or H, and X in each constituent sugar may be the same or different, the total number of X that is SO$_3$M is 6 to 10, and M has the same meaning as above.

17. A sulfated cyclic isomaltononaose or salts thereof represented by the general formula (III):

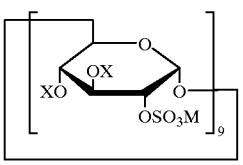

(III)

wherein X is SO$_3$M (M is a hydrogen atom, an alkali metal, an alkaline earth metal, ammonia or an organic amine) or H, and X in each constituent sugar may be the same or different, the total number of X that is SO$_3$M is 8 to 12, and M has the same meaning as above.

18. A cyclic isomaltooctaose heptadecasulfate salt wherein the total number of X that is SO$_3$M in the general formula (I) in claim 8 is 9, and M is Na or NH$_4$.

19. A pharmaceutical composition comprising the oligosaccharide or salts thereof of claim 1, 2, 3, 9, 10, 15, 16, 17, or 18 as an active ingredient.

20. A method of preparing an S-oxo group-containing oligosaccharides or salts thereof, formed of glucoses bound cyclically via α-1,6-linkages and having at least one S-oxo acid group bound thereto, comprising contacting under suitable reaction conditions a) cyclic isomaltoligosaccharide synthase or a microorganism belonging to the genus Bacillus having the ability to produce said cyclic isomaltoligosaccharide synthase with dextran to form a cyclic isomaltoligosaccharide intermediate;

b) contacting said cyclic isomaltoligosaccharide intermediate with a sulfating agent; and c) purifying said S-oxo group-containing oligosaccharides or salts thereof.

21. The method of claim 20 wherein the sulfating agent is an S-oxo acid or a sulfur trioxide adduct.

22. The method of claim 21 wherein the S-oxo acid is sulfuric acid, piperidine sulfuric acid, chlorosulfonic acid, or sulfuric anhydride; and the sulfur trioxide adduct is pyridine-SO$_3$ complex or trimethylamine-SO$_3$ complex.

23. The method of claim 20 wherein the S-oxo group-containing oligosaccharide consists of 7 to 9 glucoses.

24. The method of claim 20 wherein the S-oxo group-containing oligosaccharide has a molecular weight of between 400 to 4000.

25. The method of claim 20 wherein the S-oxo group-containing oligosaccharide has a sulfur content of 2 to 25%.

* * * * *

UNITED STATES PATENT AND TRADEMARK OFFICE
CERTIFICATE OF CORRECTION

PATENT NO. : 6,060,597
DATED : May 9, 2000
INVENTOR(S) : Koichiro Tobe et al.

It is certified that error appears in the above-identified patent and that said Letters Patent is hereby corrected as shown below:

Column 12, claim 18,
Line 3, change "claim 8" to -- claim 15 --.

Column 12, claim 20,
Line 7, change "Bacillus" to -- *Bacillus* --.

Signed and Sealed this

Twenty-fifth Day of December, 2001

Attest:

Attesting Officer

JAMES E. ROGAN
*Director of the United States Patent and Trademark Office*